(12) United States Patent
Knothe Tate et al.

(10) Patent No.: US 8,979,942 B2
(45) Date of Patent: Mar. 17, 2015

(54) MULTILAYER SURGICAL MEMBRANE

(75) Inventors: Melissa Knothe Tate, Cleveland Heights, OH (US); Ulf Knothe, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 28 days.

(21) Appl. No.: 13/581,924

(22) PCT Filed: Mar. 7, 2011

(86) PCT No.: PCT/US2011/027419
§ 371 (c)(1),
(2), (4) Date: Nov. 12, 2012

(87) PCT Pub. No.: WO2011/109817
PCT Pub. Date: Sep. 9, 2011

(65) Prior Publication Data
US 2013/0211540 A1      Aug. 15, 2013

Related U.S. Application Data

(60) Provisional application No. 61/311,056, filed on Mar. 5, 2010, provisional application No. 61/416,794, filed on Nov. 24, 2010.

(51) Int. Cl.
*A61F 2/02*    (2006.01)
*A61F 2/28*    (2006.01)
*A61B 17/56*   (2006.01)

(52) U.S. Cl.
CPC . *A61F 2/28* (2013.01); *A61B 17/56* (2013.01); *A61B 2017/561* (2013.01)
USPC ............... 623/23.72; 623/11.1; 623/16.11

(58) Field of Classification Search
USPC ............ 623/23.51, 23.52, 23.55, 23.57, 23.6, 623/23.61
See application file for complete search history.

(56) References Cited

U.S. PATENT DOCUMENTS

| | | |
|---|---|---|
| 2002/0150720 A1 | 10/2002 | Howard et al. |
| 2003/0082970 A1 | 5/2003 | Moberg-Alehammar et al. |
| 2009/0053109 A1* | 2/2009 | Tate et al. .................. 422/82.13 |
| 2009/0308404 A1 | 12/2009 | Leonard et al. |

* cited by examiner

*Primary Examiner* — Thomas J Sweet
*Assistant Examiner* — Brian Dukert
(74) *Attorney, Agent, or Firm* — Tarolli, Sundheim, Covell & Tummino LLP

(57) ABSTRACT

One aspect of the present invention relates to a multilayer surgical membrane. The surgical membrane can include a substantially fluid impermeable outer layer, an inner layer that includes a plurality of fenestrae, and a middle region disposed between the inner and outer layers. The middle region can include at least one channel that extends through the middle region. The middle region can have a first surface in contact with the inner layer. The at least one channel can imbibe fluid under a compressive or tensile load and the fenestrae can deform to exude fluid under the load.

18 Claims, 9 Drawing Sheets

Figs. 9A-B c: + autogenous periosteum-derived cell seeded collagen membrane sheets (Group 2)

d: + autogenous periosteal strips (Group 3)

e: implant sutured *in situ*

MULTILAYER SURGICAL MEMBRANE

RELATED APPLICATIONS

This application is a National Phase filing of PCT/US2011/027419, filed Mar. 7, 2011, which claims priority to U.S. Provisional Patent Application Nos. 61/311,056, filed Mar. 5, 2010, and 61/416,794, filed Nov. 24, 2010, the subject matter of which are incorporated herein by reference in their entirety.

TECHNICAL FIELD

The present invention generally relates to a multilayer surgical membrane for repairing a bone defect, and more particularly to a multilayer surgical membrane that provides vectorial delivery of endogenous periosteal factors to tissue defects.

BACKGROUND OF THE INVENTION

Critical sized diaphyseal long bone defects arising from trauma or infection, tumor, or avascular bone resection are one of the most challenging problems in orthopedic surgery. Numerous surgical techniques have been employed to treat these defects, but with limited success and a large number of complications. For example, the Ilizarov technique of distraction osteogenesis has become a standard of care for the treatment of large bone defects. Despite the success of the Ilizarov technique in treating long bone defects, however, the technique still suffers from several drawbacks, such as long and labor-intensive treatment times, significant demands on patient compliance, discomfort, and high rates of complications. The Ilizarov technique is also ineffective in the most challenging surgical cases where patients do not have sufficient periosteum to regenerate bone around critical sized bone defects, leaving surgeons with few choices to restore form and function of the patient.

SUMMARY OF THE INVENTION

This application relates to a multilayer surgical membrane for repairing a tissue defect, such as a bone defect or a soft tissue defect. The membrane can include a substantially fluid impermeable outer boundary layer, an inner layer that includes a plurality of fenestrae, and a middle region disposed between the inner and outer layers. The middle region can include and/or define at least one channel that extends through the middle region. The at least one channel can imbibe fluid under a compressive or tensile load and the fenestrae can deform to exude fluid under the load.

The present application also relates to a multilayer surgical membrane for vectorial delivery of periosteal factors from endogenous periosteum to a tissue defect, such as a bone defect. The multilayer flow directing surgical membrane can comprise a substantially fluid impermeable outer layer, an inner layer that includes a plurality of fenestrae, and a middle region disposed between the inner and outer layers. The middle region can include and/or define at least one channel that extends through the middle region. The membrane when applied to bone defect can deliver endogenous periosteal factor from endogenous periosteum under a compressive or tensile load to the bone defect to facilitate building of tissue outside/in (or inside/out) at the bone defect.

The application further relates to a surgical sleeve for repairing a bone defect in a subject. The surgical sleeve extends between a first end and a second end and can include a substantially fluid impermeable outer layer, an inner layer that includes a plurality of fenestrae, and a middle region disposed between the inner and outer layers. The middle region can include and/or define at least one channel that extends through the middle region. The sleeve when attached to engodenous periosteum at the first end and the second end and about a bone defect can deliver endogenous periosteal factor from the endogenous periosteum under a compressive or tensile load to the bone defect to facilitate building of tissue outside/in (or inside/out) at the bone defect.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 9 illustrates a schematic view of a periosteal substitute for vectorial delivery of periosteal factors to enhance defect healing. (A) The implant comprises an outer elastomeric membrane (FDA approved material), an inner elastomeric membrane with a gradient of perforations of highest concentration furthest from the proximal and distal edges of the defect zone. The layers are sewn together with suture material, creating four pockets into which periosteal factors can be tucked. (B) Collagen membranes (FDA approved) were cut and tucked into the pockets of Group 1 implants. (C) Cells were isolated from periosteum of the bone removed to create the defect, seeded on the collagen membranes (FDA approved), and tucked into the pockets of Group 2 implants. (D) Strips of periosteum were resected from bone removed to create the defect and tucked into the pockets of Group 3 implants. Bony bridging of defects sheathed by each respective periosteum substitute was compared between groups and with a control group implementing an isotropic, simple elastomeric membrane (FDA approved). (E) The periosteum substitute implant was then sutured to the proximal and distal edges of periosteum lifted along the edges of the defect and sutured close along the longitudinal axis of the lateral aspect.

DETAILED DESCRIPTION

The present invention generally relates to a multilayer surgical membrane for repairing a tissue defect, such as a bone defect or a soft tissue defect, and more particularly to a multilayer surgical membrane that provides vectorial delivery of endogenous periosteal factors to bone defects The architecture of the surgical membrane can mimic that of natural periosteum, whose vascular channels provide conduits for infiltration of growth factors and nutrients from surrounding soft tissue and whose fibrous structure provides a scaffold for rapid infiltration and proliferation of periosteum-derived cells, such as mesenchymal stem cells (MSCs). The surgical membrane can define, as one component, a flow directing material that allows for vectorial fluid flow through the membrane when the surgical membrane is subject to compression, a load causing compression, tensile stress, tension or expansion of fluid volume. In one example, the present invention harnesses physiological movement of a subject to augment directed transport of cells and nutrients from periosteum surrounding a tissue defect zone to one or more areas in direct proximity with the defect zone.

Figure 7:
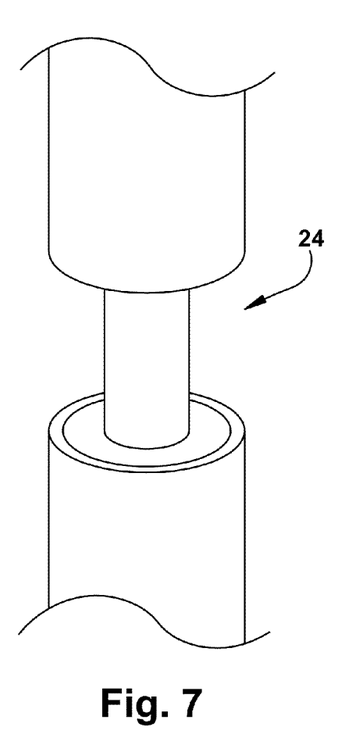
FIG. 7 is a perspective view showing a segmental bone defect.

FIGS. 1A-2B are schematic illustrations of a multilayer surgical membrane 10 in accordance with one aspect of the present invention. The surgical membrane 10 can comprise a substantially fluid impermeable outer layer 12, an inner layer 14 that includes a plurality of fenestrae 16, and a middle region 18 disposed between the outer and inner layers 12 and 14. The surgical membrane 10 can include horizontal and vertical axes 20 and 22 (FIG. 2A). Additionally, the surgical membrane 10 (FIGS. 1A-B) can have a length, a width, and a thickness that may be varied depending upon the particular application of the surgical membrane 10. For example, the surgical membrane 10 can have a sleeve-like or cylindrical configuration for application to a segmental bone defect 24 (FIG. 7), such as a diaphyseal long bone defect. Alternatively, the surgical membrane 10 (FIGS. 1A-B) can have rectangular or square-shaped configuration for application to a craniofacial bone defect, such as a bone defect in the mandible or cranium of a subject. In one example of the present invention, the surgical membrane 10 can have a thickness of about 2 cm to about 10 cm or greater, a length of about 2 cm to about 30 cm or greater, and a width of about 2 cm to about 30 cm or greater.

Figure 1A:
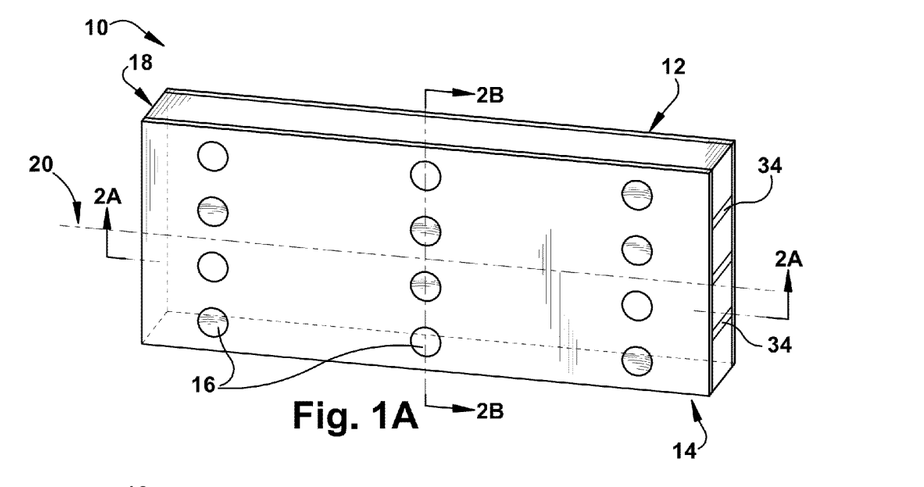
FIG. 1A is a perspective view of a multilayer surgical membrane constructed in accordance with one aspect of the present invention.
Figure 1B:
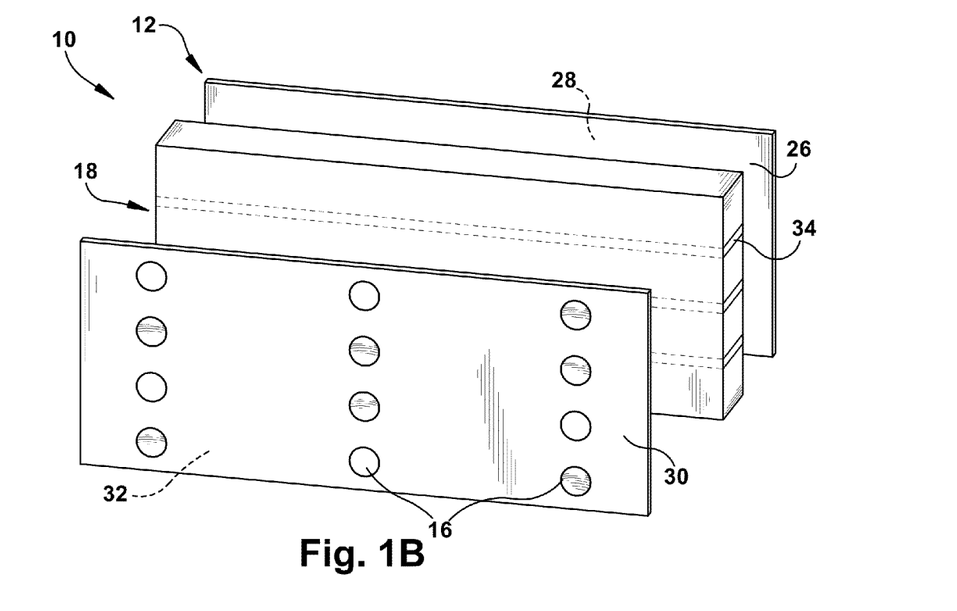
FIG. 1B is an exploded perspective view of the surgical membrane in FIG. 1A.
Figure 2A:
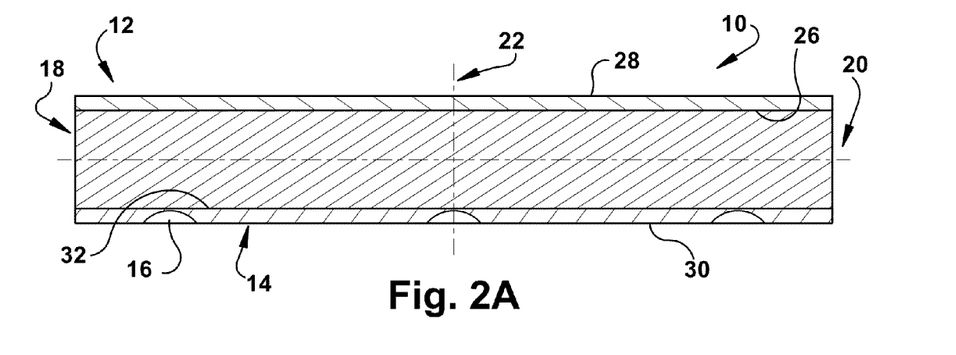
FIG. 2A is a cross-sectional view of the surgical membrane taken along Line 2B-2B in FIG. 1A.
Figure 2B:
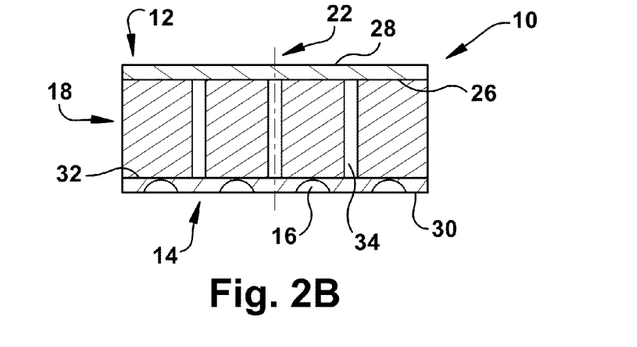
FIG. 2B is a cross-sectional view of the surgical membrane taken along Line 2A-2A in FIG. 1A.

The substantially fluid impermeable outer layer 12 of the surgical membrane 10 defines a boundary layer that can be used to prevent egression of stem cells and growth factors from the bone defect to surrounding soft tissue. The outer layer 12 can serve both sealing and mechanical energy harnessing functions. For example, the outer layer 12 can serve as a boundary layer to substantially prevent egression of periosteum-derived cells (e.g., MSCs) and growth factors from the void of a bone defect zone to the surrounding soft tissue. Additionally, the outer layer 12 is capable of withstanding strain caused by a compressive or tensile load. The outer layer 12 can comprise a thin, elastic medical grade material (e.g., silicone) having oppositely disposed first and second major surfaces 26 and 28 that extend substantially parallel to the horizontal axis 20. The outer layer 12 can have any desired length, width and thickness. For example, the outer layer 12 can have a length of about 2 cm to about 30 cm or greater, a width of about 2 cm to about 30 cm or greater, and a thickness of about 1 cm to about 4 cm or greater.

The inner layer 14 of the surgical membrane 10 can comprise a thin, elastic medical grade material (e.g., silicone) having oppositely disposed first and second major surfaces 30 and 32 that extend substantially parallel to the horizontal axis 20. The inner layer 14 can additionally include a plurality of fenestrae 16 that modulate fluid flow through the first major surface 30. The size, shape, number (i.e., porosity), and distribution of fenestrae 16 can be varied to modulate fluid flow through the first major surface 30. Upon application of a compressive or tensile load to the second major surface 28 of the outer layer 12, the fenestrae 16 can deform (e.g., expand) to allow fluid flow through the first major surface 30. For example, the fenestrae 16 can deform to allow for penetration of periosteum-derived cells (e.g., MSCs), nutrients, and/or growth factors into a bone defect zone upon application of a compressive or tensile load to the second major surface 28 of the outer layer 12. The inner layer 14 can have any desired length, width, and thickness. For example, the inner layer 14 can have a length of about 2 cm to about 30 cm or greater, a width of about 2 cm to about 30 cm or greater, and a thickness of about 1 cm to about 4 cm or greater.

The porosity of the inner layer 14 (e.g., void volume of a respective region in $mm^3$/total volume of a respective region in $mm^3$) can be about 0.1 to about 0.9. Although the fenestrae 16 are shown as having a circular cross-sectional profile, it will be appreciated that the fenestrae 16 can have any desired cross-sectional profile (e.g., ovoid, square, rectangular, etc.), and that all or only a fraction of the fenestrae 16 can have the same cross-sectional profile. The diameter of the fenestrae 16 can range from less than about 1 µm to about 1 mm or more, and all or only a fraction of the fenestrae 16 can have the same diameter. The fenestrae 16 can be uniformly spaced apart or, alternatively, arranged in a gradient about the inner layer 14. For example, the inner layer 14 can include a central region flanked by opposing outer regions, wherein the central region has a porosity that is greater than the porosity of each of the outer regions. The fenestrae 16 can be formed by known micro-fabrication or nano-fabrication techniques, such as laser cutting.

Figure 3A:
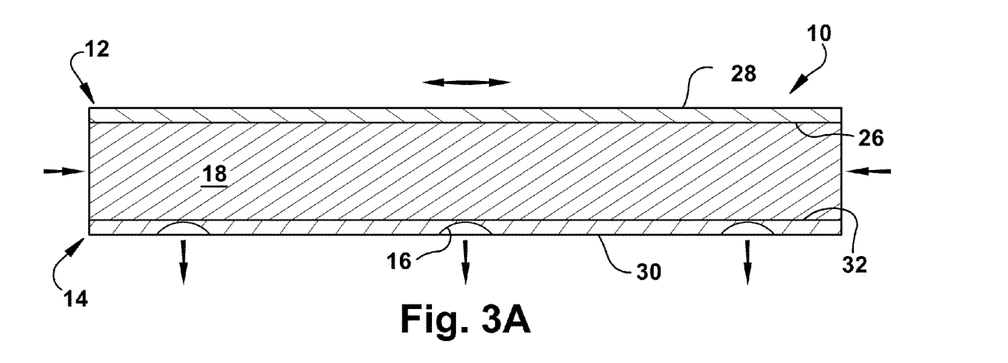
FIG. 3A is a cross-sectional view of the surgical membrane in FIG. 2A under a compressive or tensile load (indicated by double arrow)
Figure 3B:
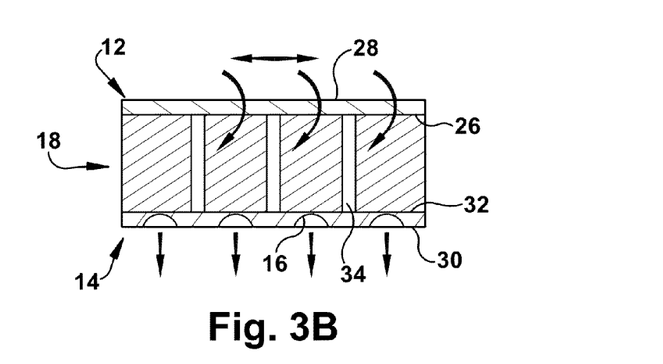
FIG. 3B is a cross-sectional view of the surgical membrane in FIG. 2B under a compressive or tensile load (indicated by double arrow)

The middle region 18 of the surgical membrane 10 can be disposed (e.g., sealed) between the outer and inner layers 12 and 14 and/or defined by the outer and inner layers 12 and 14. For example, the middle region 18 can be sealed between the outer and inner layers 12 and 14 using nano-micro welding techniques. The spatial distribution of the welds can create channels 34 or conduits that extend the length of the middle region and that mimic the natural vasculature of the periosteum. As shown in FIGS. 3A-B, the channels 34 can allow for infiltration of growth factors and/or nutrients from surrounding soft tissue. Additionally, the middle region 18 can include a fibrous structure that provides a scaffold for rapid infiltration and proliferation of periosteum-derived cells, such as MSCs. As described in more detail below, the middle region 18 can harness pressure differentials occurring during natural physiological movement to pump interstitial fluid from the surrounding periosteum into a bone defect zone.

Figure 4A:
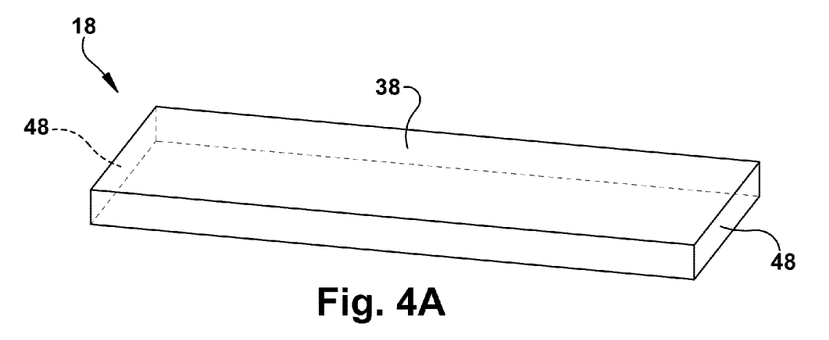
FIG. 4A is a perspective view showing a middle layer of the surgical membrane in FIGS. 1A-B.
Figure 4B:
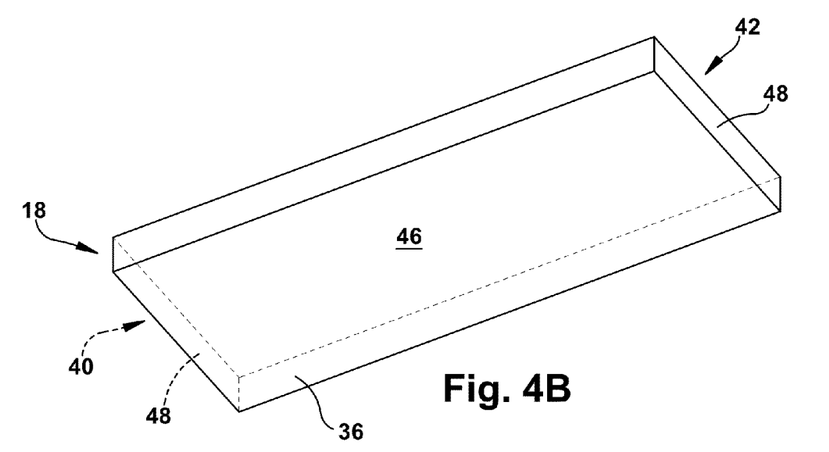
FIG. 4B is a different perspective view of the middle layer in FIG. 4A.

In an aspect of the application, the middle region 18 (FIGS. 4A-B) can include a layer that is defined by oppositely disposed first and second major surfaces 36 and 38, as well as oppositely disposed first and second minor surfaces 40 and 42. In one example of the present invention, the middle region 18 can be configured as a single sheet as shown in FIGS. 4A-B. In this configuration, the middle region 18 can have any desired length, width, and thickness (e.g., a length of about 2 cm to about 30 cm or greater, a width of about 2 cm to about 30 cm or greater, and a thickness of about 1 cm to about 4 cm or greater).

Figure 5:
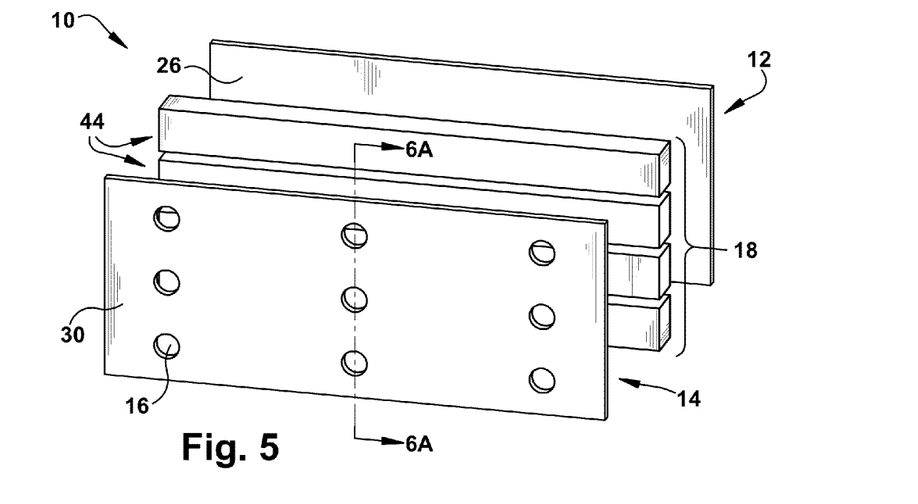
FIG. 5 is an exploded perspective view of a multilayer surgical membrane constructed in accordance with another aspect of the present invention, with modules (44) stacked along the length of the inner and outer layer.

In another example of the present invention, the middle region 18 can alternatively comprise a series of modules 44 (FIG. 5). Each of the modules 44 can have any desired length, width, and thickness. For example, all or only one of the modules 44 can have a length of about 2 cm to about 30 cm or greater, a width of about 1 cm to about 15 cm or greater, and a thickness of about 1 cm to about 4 cm or greater. It will be appreciated that each of the modules 44 can be equally or differently sized as compared to the other modules 44.

In another aspect of the application, the middle region 18 can be formed from a flow directing material that is similar or identical to the flow directing material disclosed in U.S. patent application Ser. No. 12/106,748 to Knothe Tate et al., the entirety of which is hereby incorporated by reference. The flow directing material has a porous structure and is capable of being compressed when a load is applied to the second major surface 28 of the outer layer 12. By way of example, the flow directing material can be formed of a porous compliant polymeric foamed material, a porous compliant nano-engineered material, and/or a porous compliant biological material.

The first major surface 36 of the middle region 18 can include an exuding region 46 that is in communication with the fenestrae 16. The exuding region 46 is capable of exuding fluid when a load causing compression is applied to the outer layer 14 of the surgical membrane 10. Each of the first and second minor surfaces 40 and 42 of the middle region 18 can include an imbibing region 48 that is capable of imbibing fluid when a load is applied to the outer layer 12. As shown in FIGS. 4A-B, the exuding region 46 and the imbibing regions 48 can be adjacent to or about one another.

The exuding region 46 can have a first porosity, and each of the imbibing regions 48 can have a second porosity. The porosities (or porosity ratio (e.g., void volume of the respective region in $mm^3$/total volume of the respective region in $mm^3$)) of the exuding region 46 and the imbibing regions 48 can be about 0.3 and about 0.7, respectively. The porosities of the exuding region 46 and the imbibing regions 48 can also be at least about 5% different so that the direction of fluid flow in and/or through the exuding region 46 will be different than (e.g., contrary, opposite, and/or substantially normal to) the direction of fluid flow in and/or through the imbibing regions 48. That is, the difference of porosities of the exuding region 46 and the imbibing regions 48 can determine, at least in part, the direction of fluid flow in and/or through the exuding region 46 and the imbibing regions 48.

The exuding region 46 and the imbibing regions 48 can also have, respectively, a first permeability and a second permeability. The permeabilities of the exuding region 46 and the imbibing regions 48 can be about $10^{-13}$ $m^2$ to about $10^5$ $m^2$. The permeability can control the magnitude of fluid flow in the flow directing material when the flow directing material is under compression, and can potentially control the timing of transport of fluid depending on the specific application of the flow directing material. In one aspect, the exuding region 46 can have substantially the same permeability as the imbibing regions. In another aspect, the exuding region 46 and the imbibing regions 48 can have different permeabilities.

The surgical membrane 10 can exude fluid from the exuding region 46 and imbibe fluid from the imbibing regions 48 when a load is applied to the second major surface 28 of the outer layer 12 so as to compress the surgical membrane 10. The load or compression need not occur substantially normal to the horizontal axis 20 to cause the exuding region 46 to exude fluid and the imbibing regions 48 to imbibe fluid. The load can be applied at any angle relative to the horizontal axis 20 as long as the flow directing material is compressed. The load need not be compressive but can also be tensile. Tensile loads can be applied, for example, in a plane extending substantially parallel to the horizontal axis 20, resulting in a shortening of fenestrae 16 heights in accordance with Poisson's effect. In addition to this effect, tensile loads can be applied normal to the second major surface 28 of the outer layer 12, which would expand fenestrae 16 volumes, resulting in equal but opposite flows for areas of exudation and imbibition for a tensile load that is equal but opposite to a given compressive load.

The exuding region 46 and the imbibing regions 48 can be formed from flexible or compliant polymeric foams having, respectively, a first porosity and a second porosity. The polymeric foams can include those that are substantially open-celled. The cells in such substantially open-celled foam structures can have intracellular openings or windows that are large enough to permit ready fluid transfer from one cell to the other within the regions. These substantially open-celled foam regions will generally have a reticulated character with the individual cells being defined by a plurality of mutually connected, three dimensionally branched webs.

The polymers used to form the polymeric foam can comprise any polymer that is capable of being foamed or provided with an open-celled structure. Examples of polymers that can be used to form the polymeric foam include elastomers, expanded polytetrafluoroethylene, polypropylene, nylon, hydrophilic polystyrene foams, styrene butadiene styrene, methyl vinyl ether, maleic anhydride, GoreTex, and biopolymers, such as collagen, collagen modified with chondroitin sulfate, cellulose, hydroxypropyl methylcellulose, ethyl cellulose, and chitin. It will be appreciated that the flow directing material can be formed from other flexible or compliant materials besides polymeric foams. These other materials can include, for example, nano-scale, meso-scale, or micro-scale engineered composites or matrices in which the porosity and the permeability of the material is controlled, as well as biological materials with native or engineered porosities and permeabilities.

The flow directing material can be loaded or imbibed with one or a combination of molecules and/or cells that promote bone growth. For example, the flow directing material can be imbibed with trophic factors, such as growth factors (e.g., BMP-7, BMP-4, BMP-2, PDGF-BB, TGF-β1, tetracycline, bFGF, VEGF, PTH, and PTH-rp). Examples of cells that can be imbibed in the flow directing material can include periosteum-derived cells, such as autogenic stem cells (e.g., MSCs). It will be appreciated that other molecules, such as carbohydrates, nucleic acids, small molecules, proteins, and/or polypeptides can also be imbibed in the flow directing material.

Figure 6A:
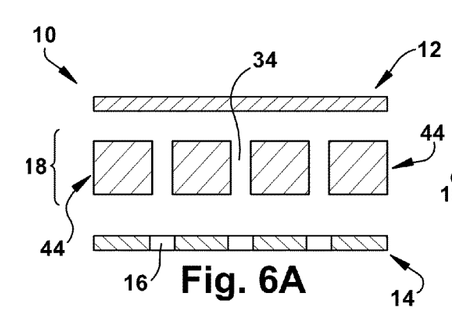
FIG. 6A is a cross-sectional view of the surgical membrane taken along Line 6A-6A in FIG. 5.
Figure 6B:
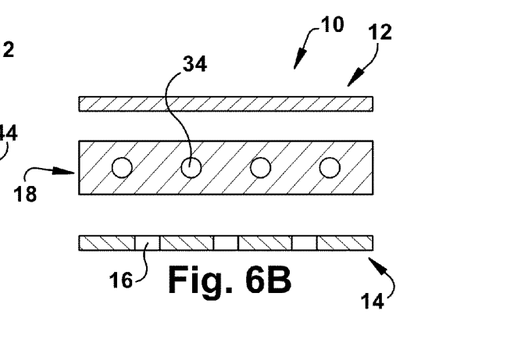
FIG. 6B is a cross-sectional view showing an alternative construction of the surgical membrane in FIG. 6A.
Figure 6C:
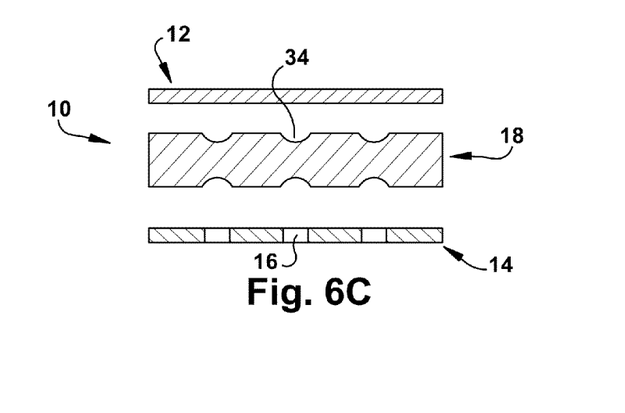
FIG. 6C is a cross-sectional view showing another alternative construction of the surgical membrane in FIG. 6A.

In another aspect, the middle region 18 can include at least one channel 34 or conduit extending partly or entirely between the first and second minor surfaces 40 and 42 of the middle region 18. The channels 34 can have any desired cross-sectional profile, such as a rectangular (FIGS. 1A-B) or circular (FIG. 6B) cross-sectional profile. The channels 34 can be separately formed by virtue of the welds between modules 44 (FIG. 6A), completely formed (e.g., bored)

within the middle region 18 (FIG. 6B), or partially formed within the middle region 18 (FIG. 6C). The channels 34 can be in direct communication with the fenestrate 16. Alternatively, the channels 34 can be in indirect communication with the fenestrae 16 via the interconnected open cells that comprise the flow directing material. The size, shape, number, and distribution of the channels 34 can be varied to modulate fluid flow through the middle region 18.

In one example of the present invention, the surgical membrane 10 can include an outer layer 12 made of medical grade silicone, an inner layer 14 formed from medical grade silicone, and three modules 44 sealed between the outer and inner layers 12 and 14. Each of the modules 44 can include collagen. The modules 44 can be sealed within the outer and inner layers 12 and 14 via nano-micro welding methods. The welds can serve as channels 34, which mimic the vasculature of the natural periosteum.

In another example, the surgical membrane 10 can include an outer layer 12 formed from an impermeable elastic sheet and an inner layer 14 formed from a sheet of collagen type I. The middle region 18 can have a multilayered configuration and comprise: a first layer that is in contact with the outer layer 12 and made of collagen type I and imbibed with nutrients, angiogenic factors, and Notch; a second layer that is comprised of collagen type I and contains a plurality of channels designed to imbibe fluid from the first and second minor surfaces of the middle region under cyclic tension; a third layer comprising collagen type I; a fourth permeable layer having fenestrae to modulate temporal release of imbibed molecules from the layers toward the bone defect zone; a fifth layer comprised of a collagen sponge, which serves as a larger depot for nutrients, angiogenic factors, and Notch; and a sixth layer comprised of a fibronectin sheet, which is in contact with the inner layer 14 and upon which cells (e.g., MSCs) can be seeded.

The surgical membrane 10 can be used in a variety of orthopedic procedures where repair of a bone defect is needed and where vectorial delivery of bone repair agents, including endogenous periosteal factors is desired. Orthopedic injuries, such as segmental bone defects can be caused by a variety factors, including trauma (e.g., combat, accidents), infection, tumor, and avascular bone resection. With such injuries, there is often an insufficient amount of periosteum around the bone defect to promote new bone growth and thus proper bone repair and healing. The surgical membrane 10 of the present invention can be used as replacement periostea for surgical reconstruction procedures.

As described above, the architecture of the surgical membrane 10 mimics that of the periosteum, whose vascular channels provide conduits for infiltration of growth factors and nutrients from the surrounding soft tissue and whose fibrous structure provides a scaffold for rapid infiltration and proliferation of MSCs. By suturing the surgical membrane 10 to healthy periosteum surrounding (but not sufficient to cover) critical bone defect zones, the surgical membrane 10 provides a continuous layer, linking areas of healthy periosteum to the bone defect zone. In this way, the surgical membrane 10 provides a bridge and conduit, which enables targeted delivery of cells and molecules (e.g., growth factors and nutrients) from healthy periosteum into the bone defect zone.

Figure 8:
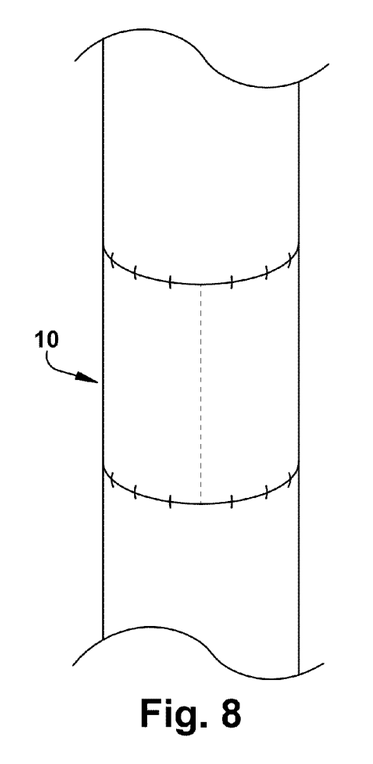
FIG. 8 is a perspective view showing a sleeve-shaped surgical membrane of the present invention affixed to the segmental bone defect.

In one example of the present invention, the surgical membrane 10 can be used to repair a bone defect, such as a segmental bone defect 24 (FIG. 7) in a subject. To repair the segmental bone defect 24, the surgical membrane 10 can be configured to have a sleeve-like or cylindrical configuration. The surgical membrane 10 can be implanted about the segmental bone defect 24 using the one-stage surgical procedure disclosed by Knothe Tate M L et al., *J Bone Joint Surg (Br)* 89(2):307-316 (2007). The procedure exploits the intrinsic osteogenic potential of the periosteum while providing mechanical stability through intramedullary nailing. As shown in FIG. 8, the surgical membrane 10 can be sutured to healthy periosteum surrounding (but not sufficient to cover) the bone defect zone 24 to provide a continuous layer, linking areas of healthy periosteum to defect 24.

When the surgical membrane 10 is under tension (e.g., during physiological movement of the subject), the fenestrae 16 of the inner layer 14 can deform (e.g., expand) so that fluid exiting the exuding region 46 carries cells (e.g., MSCs) that reside in the surrounding healthy periosteum into the bone defect zone 24 (i.e., through the expanded fenestrae 16). When the surgical membrane 10 relaxes, the diameter of each of the fenestrae 16 can return to its original size. Hence, when the pressure gradient relaxes, fluid can be imbibed back into the middle region 18 and the cells can remain in the defect zone 24 to proliferate and generate woven bone. In this way, the surgical membrane 10 can harness the small strains occurring during locomotion or movement to pump fluids to and from the bone defect zone 24, thereby enhancing not only mass transport to and from the defect 24, but also transport of cells into the bone defect zone 24. This allows the sleeve to deliver endogenous periosteal factor from endogenous periosteum under a compressive or tensile load to the bone defect to facilitate building of tissue outside/in at the bone defect.

EXAMPLE

Figure 9A:
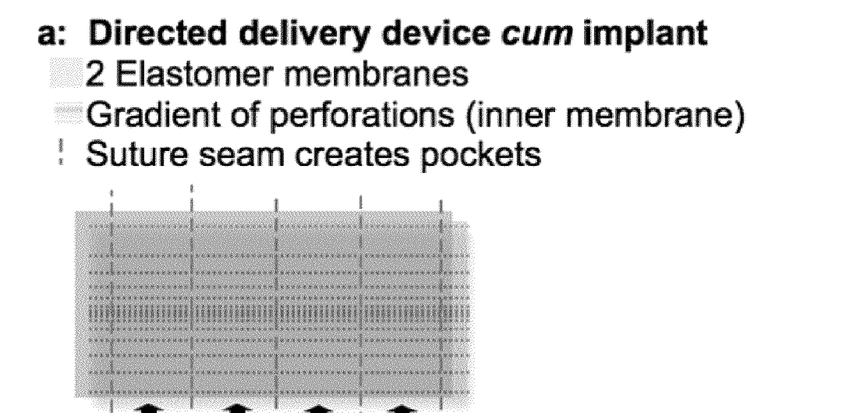
Figure 9B:
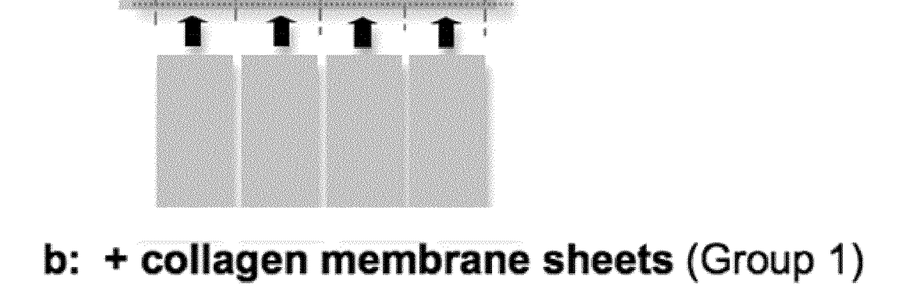
Figure 9C:
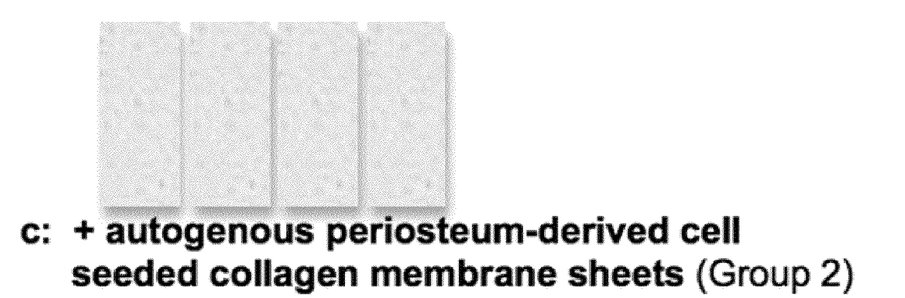
Figure 9D:
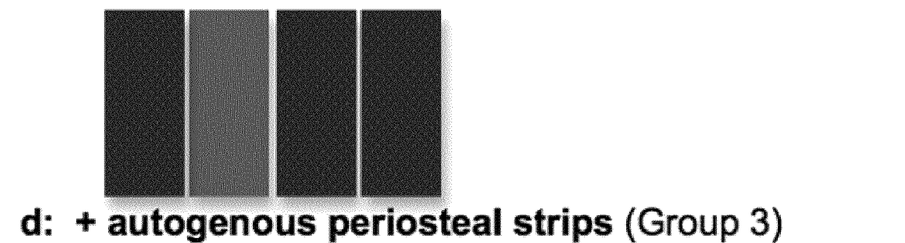
Figure 9E:
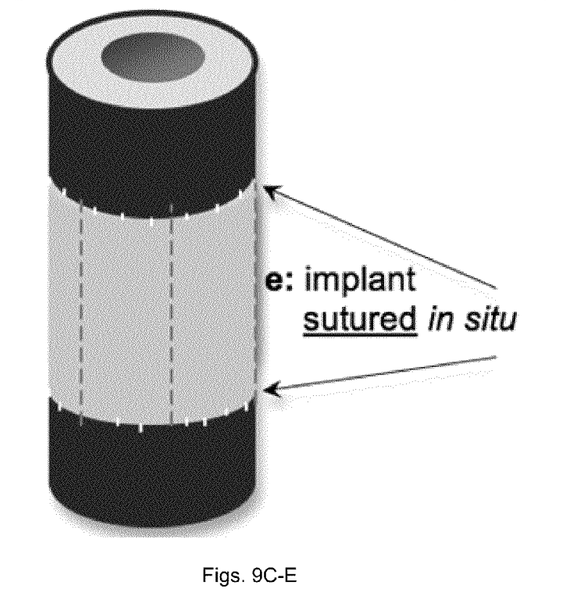

In this example, we implemented a newly developed surgical reconstruction membrane as a substitute for the periosteum to treat a critical sized (2.54 cm) defect in a previously developed adult ovine femur model with intramedullary nailing for mechanical stabilization. The periosteum substitute serves as a delivery device cum implant and exhibits a modular design with pockets to allow for spatial and temporal control of factor delivery (FIG. 9A). Here we used the periosteum substitute for the controlled addition of periosteal factors including vectorial transport afforded by the membrane architecture per se, the presence of collagen in the periosteum (FIG. 9B, Group 1), cells residing within the periosteum (FIG. 9C, Group 2), and other biologic factors instrinsic to the periosteum (FIG. 9D, Group 3).

Previously described surgical protocols were used to create critical sized, middiaphyseal femur defects[5], first in one short term (3 week) pilot group treated with periosteum substitute implants incorporating collagen membranes (Group 1). Thereafter, we treated four groups of five skeletally mature Swiss alpine sheep for sixteen weeks, a period over which defects surrounded by periosteum in situ heal completely and untreated defects do not heal (providing proof of critical size).

Each group was treated using a substitute periosteal membrane designed and manufactured according to our protocols to deliver specific factors to the defect zone (FIG. 9, Table 1). The substitute periosteum implants comprised combinations of FDA-approved materials and/or autologous materials including periosteum derived cells and periosteal strips from the bone removed to create the defect. The FDA approved materials used to make the implants included medical grade silicone elastomer sheeting, absorbable collagen membrane derived from bovine achilles tendon, and nonresorbable sutures (FIG. 9). The periosteum substitutes were designed to be easily manufactureable, modular (the pocket design allows for substitution as well as precise localization and timing the release of specific factors or combinations of factors), fully sterilizable with other surgical armementaria, and easy to use by surgeons with varying degrees of expertise.

To create the modular design, an inner membrane was first perforated with a gradient of holes along its entire length, with the highest concentration of holes near the center of the defect region, decreasing toward the edges that are sutured to the periosteum of healthy bone proximal and distal to the defect zone. The pattern of holes was achieved using a double (parallel) sewing machine needle (without thread) and setting the sewing machine stitch length to achieve equidistance at the center of the defect between rows of double holes. The inner membrane was then sewn, using the suture material, to the outer membrane, which was devoid of perforations, creating a long sleeve (3.5×10 cm) with four 2 cm wide pockets (FIG. 9A-B). The whole construct was then placed on surgical dressing gauze and encapsulated within a sterilization sleeve for steam sterilization in an autoclave with other surgical instrumentarium.

Shortly before surgical implantation (in the sterile surgical operating theatre), the substitute periosteum implant was removed from the sterile packaging and experimental (periosteal) factors were placed in the implant pockets (collagen membrane—Group 1, collagen membrane seeded with autogenous periosteum derived cells—Group 2, or strips of autogenous periosteum transplants from bone removed to create defect—Group 3, Table 1). The implant was then sutured to periosteum lifted along the edge of the remaining bone proximal and distal to the defect (FIG. 2D). The control group was treated with a simple, isotropic silicone elastomer membrane (without flow directing architecture) around the critical sized defect. Group 1 was treated with a membrane and collagen sheets, incorporating flow directing architecture which allows for vectorial transport from the proximal and distal edges axially toward the center, and from the membrane radially toward the intramedullary nail. Group 3 received the membrane as in Group 2, but the collagen sheet within the membrane was pre-seeded with cells isolated from periosteum of the autologous defect bone and incubated at 37° C. overnight. After careful aspiration and washing, the cell-seeded membrane was then placed into the four pockets of the substitute periosteum. Finally, Group 4 received the membrane in combination with autologous periosteal transplant strips (isolated from the bone removed to create the defect zone) in place of the collagen sheets.

TABLE 1

| Groups | 0-25% | 25-50% | 50-75% | 75-100% |
| --- | --- | --- | --- | --- |
| EMPTY | 7/7 | | | |
| control membrane | 4/5 | 1/5 | | |
| Membrane + collagen | 5/5 | | | |
| Membrane + collagen + cells | 1/5 | 2/5 | 1/5 | 1/5 |
| Membrane + periosteal strips | | 2/5 | 1/5 | 2/5 |
| INTACT PERIOSTEUM | | | | 7/7 |

Animals were euthanized at 3 (pilot group) and 16 weeks after surgery. Femoral tissue blocks including surrounding musculature were scanned with the intramedullary (IM) nail in situ using high resolution μ-CT to determine efficacy of the periosteal substitutes for defect bridging. Due to the retention of the steel IM nail (which can cause imaging artifacts due to beam hardening), it was not possible to obtain volumetric data from the μ-CT images. For this reason, bridging of the defect was ranked on a quartile scale (Table 1, 0-25%, 25-50%, 50-75%, 75-100%), indicating degree of defect coverage for each treated sample in each experimental group.

Figure 10:
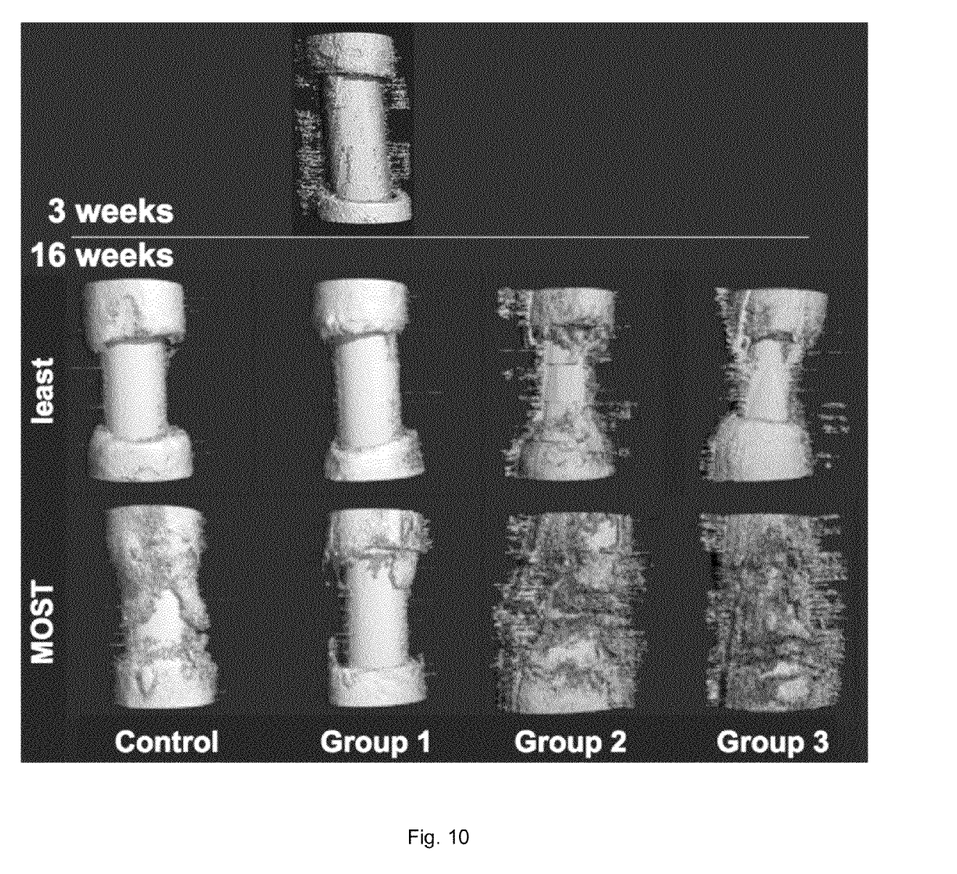
FIG. 10 illustrates high resolution micro-computed tomography images of bone regenerate in Group 1 at 3 weeks and in all groups at 16 weeks after surgery. The intramedullary nail is present along the longitudinal axis of all specimens. Each group comprised five sheep and the sample images showing the least and most amount of new bone are depicted for each group.

Micro-computed Tomography (μ-CT) data show that membranes incorporating periosteal factors (Group 4>Group 3>control) improve bone regeneration compared to isotropic, unstructured control membranes made of the same material (Table 1, FIG. 10). At three weeks after treatment with periosteum substitute implants incorporating collagen sheets (Group 1), membranous bone was observed emanating from the implant toward the intramedullary nail. This intramembranous bone was no longer observable at sixteen weeks. In fact, at 16 weeks, Group 1 did not show increased defect filling compared to the isotropic control membrane. Insertion of collagen sheets seeded with periosteal derived cells (Group 2) within the periosteum substitute implant increased defect bridging compared to the isotropic control membrane (control) as well as the periosteum substitute with collagen sheets (Group 1). Maximal bone infilling of the defect was observed in Group 3, where autologous strips of periosteum were tucked into the pockets of the modular periosteum substitute.

The current set of experiments indicate a key role for periosteum-derived cells as well as other factors intrinsic to periosteal transplants for infilling of critical sized defects. Previously published studies have underscored the need to engineer periosteum substitutes but have met with limited success in bridging critical sized defects. In trauma patients, as well as in surgical reconstruction patients, the amount of remaining healthy periosteum represents a limit to the use of the endogenous engineering approach demonstrated to bridge critical sized defects in the ovine femur (one-stage bone-transport procedure). The current studies implementing the newly developed periosteal substitutes, augmented through addition of periosteal transplant from other bone sites, test the use of the technology as a delivery vehicle for the patient's endogenous bone healing factors, expanding the indications for surgical reconstruction sheets in treatment of long bone defects. In addition, the periosteal substitutes, enhanced through seeding with autogenous stem cells harvested from periosteum, further expand the use of the technology for a range of tissue defects.

Methods

Sheep and Surgical Procedures

The experimental protocol was carried out, using skeletally mature Swiss alpine sheep (n=5 per group, 3 experimental and one control group), at the AO Research Institute in Davos, Switzerland, with the approval of the animal care and use commission of the Canton of Grisons.

All surgeries were performed by URK. Surgery was performed with sheep in the right lateral position. After general anaesthesia with intubation and spinal anaesthesia, the left hindlimb was shaved and prepped with Hibiscrub solution and draped. The right hind limb was strapped with a belt extending around the operating table and the abdomen. The sheep was then transported into the operating room and the left hind limb was prepped and draped in the usual sterile fashion. A lateral parapatellar approach was performed to enter the knee joint to prepare for retrograde IM nailing. The patella was dislocated medially. A 4 mm entry hole was then placed in the midline of the trochlea approximately 8 mm anterior to the intracondylar notch. Sequential reaming of the intramedullary canal was performed with increasing sized cutting reamers, starting at 7 mm, going up to 14 mm. The flexible Synthes reamer system was then used to ream 15 mm, up to 16 mm, in 0.5 mm increments.

Attention was then turned lateral to the femur and a second, approximately 12.5 cm incision was made lateral over the femur. The vastus lateralis fasciae and the intramuscular plane were developed to expose the lateral aspect of the femur. Meticulous hemostasis and ligation of larger vessels was performed, distal third of the femur. The vastus lateralis was then detached from the bone with a scalpel to expose the distal femur with a 1-2 mm layer of muscle attached. A 2.54 cm critical sized defect was then created 8 cm proximal to the knee joint line with an oscillating saw using small amplitude and preserving the soft tissue with rounded custom retractors.

The periosteum was then lifted circumferentially, approximately 5 mm from the proximal and distal defect/osteotomy edges, with a periosteal elevator. The intramedullary nail was then inserted retrograde and care was taken to maintain the 2.5 cm critical defect size. Two proximal and two distal 4.9 mm interlocking bolts were then placed.

The 3.5 cm periosteum substitute membrane was then introduced around the defect using a custom S-shaped retractor to maintain space medial to the femur-nail. The membrane was placed from anterolateral side and brought posterior around the defect. The membrane was designed to overlap 0.5 cm distal and proximal to the defect. In the case of the experimental membrane, the outer layer overlapped the elevated periosteum by 5 mm and the inner layer was placed so that the periosteum was sandwiched between and sutured carefully in place with Dermalon 4.0 sutures, while applying inner and outer rotation of the hind limb as needed to reach regions behind the IM nail. In the case of the simple control membrane, the membrane was placed overlapping the elevated periosteum by 5 mm and sutured in place. The edges of the membrane were connected laterally using Dermalon 4.0 sutures and trimmed to fit the circumference of the defect.

The knee and lateral femoral incisions were then closed in layers with no suction tube trains, using vicryl #1 for fascia, 2.0 for subcutaneous and Moncryl 3.0 for subcuticular running sutures.

Implant Manufacture

Substitute periosteal membrane were designed and manufactured as sterilizable, modular units to deliver specific factors to the defect zone. Delivery devices (modular implant with pockets) were manufactured from FDA materials, including medical grade silicone sheeting (Bioplexus, 0.005" thick medium durometer silicone elastomer, Ventura, Calif.), and nonresorbable sutures (Dermalon 4-0, monofilament nylon, Syneture, Covidien Surgical, Dublin, Ireland). Absorbable collagen membrane (Biomend®, derived from bovine achilles tendon, Zimmer Dental, Carlsbad, Calif.), designed for periodontal use, were placed in implant pockets in Groups 1 (collagen membrane alone) and 2 (collagen membrane seeded with cells isolated from autologous periosteum). Autologous periosteal strips were placed in the pockets of implants from Group 3. Unaltered, isotropic medical grade silicone sheets were used in the control group. Bone growth within implants incorporating increasing numbers of periosteal factors were compared with control implants as well as with the baseline critical sized defect control (untreated) and "gold standard" in situ periosteum treatment studied previously.

Cell Culture Methods—Isolation and Proliferation of Periosteum Derived Cells

Ovine periosteum explants resected from the bone removed to create the defect are immediately placed in TBSS with 1% Penicillin/Streptomycin (P/S). The explants are then minced and placed in spinner flasks with high glucose DMEM (GIBCO, Grand Island, N.Y.) with 1% P/S and 0.3% Collagenase II (Worthington Biochemical Corporation, Lakewood, N.J.). This is incubated for 3 hours in a 37° C. incubator in 95% humidified air and 5% $CO_2$. The cells were filtered through a 40 mm filter, centrifuged and seeded on the precut collagen membranes, which are sized to fit into the periosteal implant pockets. The seeded membranes are then incubated overnight at 37° C., in 95% humidified air with 5% $CO_2$. The next morning, after careful aspiration and washing, the seeded membranes are then placed into the four pockets of the substitute periosteum implant, under sterile conditions in the surgical theater.

We characterized growth rates of the ovine periosteum derived cells prior to the current study. Adherent periosteum derived cells were plated at 34,000 cells/$cm^2$ high sets of 8 in 96-well plates in high glucose DMEM with 10% FBS and 1% P/S. Cell culture media was changed every 2-3 days. Cell numbers were analyzed for 22 days using WST-1 reagent (Roche Applied Science, Indianapolis, Ind.) incubated for 4 hours before measuring absorbance From the above description of the invention, those skilled in the art will perceive improvements, changes and modifications. For example, it will be appreciated that the surgical membrane 10 can be used to treat craniofacial bone defects, such as defects in the cranium and mandible. Such improvements, changes, and modifications are within the skill of the art and are intended to be covered by the appended claims.

Having described the invention, the following is claimed:

1. A multilayer surgical membrane comprising:
   a substantially fluid impermeable outer layer;
   an inner layer including a plurality of fenestrae; and
   a middle region disposed between the inner and outer layers, the middle region including at least one channel that extends through and/or is defined by the middle region;
   wherein the at least one channel imbibes fluid under a compressive or tensile load and the fenestrae deform to exude fluid under the load.

2. The multilayer surgical membrane of claim 1, the plurality of fenestrae modulating fluid flow through the middle region.

3. The multilayer surgical membrane of claim 1, the inner layer including a central region flanked by opposing outer regions, the central region having a porosity greater than the porosity of each of the outer regions.

4. The multilayer surgical membrane of claim 1, the inner layer including a central region flanked by opposing outer regions, the central region having a porosity that is the same as the porosity of each of the outer regions.

5. The multilayer surgical membrane of claim 1, the middle region having a structure of interconnected open cells.

6. The multilayer surgical membrane of claim 1, the middle region including a flow directing material.

7. The multilayer surgical membrane of claim 1, the middle region comprising a plurality of modules spaced apart by the at least one channel.

8. The multilayer surgical membrane of claim 1, the middle region including at least one periosteum-derived cell.

9. A multilayer surgical membrane for vectorial delivery of periosteal factors from endogenous periosteum to a bone defect comprising:
   a substantially fluid impermeable outer layer;
   an inner layer including a plurality of fenestrae; and
   a middle region disposed between the inner and outer layers, the middle region comprising at least one channel that extends through the middle region, the membrane when applied to a bone defect delivering under a compressive or tensile load to the membrane endogenous periosteal factors from endogenous periosteum to the bone defect to facilitate building of tissue at the bone defect;
   wherein the at least one channel imbibes fluid under a compressive or tensile load and the fenestrae deform to exude fluid under the load.

10. The multilayer surgical membrane of claim 9, the inner layer including a central region flanked by opposing outer regions, the central region having a porosity greater than the porosity of each of the outer regions.

11. The multilayer surgical membrane of claim 9, the inner layer including a central region flanked by opposing outer regions, the central region having a porosity that is the same as the porosity of each of the outer regions.

12. The multilayer surgical membrane of claim 9, the middle region having a structure of interconnected open cells.

13. The multilayer surgical membrane of claim 9, the middle region comprising a plurality of modules spaced apart by the at least one channel.

14. The multilayer surgical membrane of claim 9, the middle region including at least one periosteum-derived cell.

15. A surgical sleeve for repairing a bone defect in a subject, comprising:
a multilayer membrane that extends between a first end and a second end, the multilayer membrane including a substantially fluid impermeable outer layer, an inner layer including a plurality of fenestrae, and a middle region disposed between the inner and outer layers that includes or defines at least one channel, the sleeve delivering endogenous periosteal factor from endogenous periosteum under a compressive or tensile load to the bone defect to facilitate building of tissue at the bone defect;
wherein at least one channel imbibes fluid under a compressive or tensil load and the fenestrae deform to exude fluid under the load.

16. The multilayer surgical membrane of claim 15, the plurality of fenestrae modulating fluid flow through a first surface of the middle region.

17. The multilayer surgical membrane of claim 15, the inner layer including a central region flanked by opposing outer regions, the central region having a porosity greater than the porosity of each of the outer regions.

18. The multilayer surgical membrane of claim 15, the inner layer including a central region flanked by opposing outer regions, the central region having a porosity that is the same as the porosity of each of the outer regions.

* * * * *